United States Patent
Hocken et al.

(10) Patent No.: US 10,240,984 B2
(45) Date of Patent: Mar. 26, 2019

(54) TEMPERATURE MEASUREMENT METHOD FOR A HEATED SENSOR

(75) Inventors: Lary R. Hocken, Davison, MI (US); Charles S. Nelson, Fenton, MI (US)

(73) Assignee: DELPHI TECHNOLOGIES, INC., Troy, MI (US)

( * ) Notice: Subject to any disclaimer, the term of this patent is extended or adjusted under 35 U.S.C. 154(b) by 1077 days.

(21) Appl. No.: 13/432,123

(22) Filed: Mar. 28, 2012

(65) Prior Publication Data

US 2013/0256296 A1    Oct. 3, 2013

(51) Int. Cl.
  *H05B 1/02*    (2006.01)
  *G01K 7/16*    (2006.01)
  *G01N 15/06*   (2006.01)
  *G01N 15/00*   (2006.01)

(52) U.S. Cl.
  CPC ........... *G01K 7/16* (2013.01); *G01N 15/0656* (2013.01); *G01K 2217/00* (2013.01); *G01N 2015/0046* (2013.01)

(58) Field of Classification Search
  CPC .. G01K 7/16; G01K 2217/00; G01N 15/0656; G01N 2015/0046
  USPC ................. 219/482, 497; 73/23.33, 28.01
  See application file for complete search history.

(56) References Cited

U.S. PATENT DOCUMENTS

| | | | |
|---|---|---|---|
| 4,656,832 A | 4/1987 | Yukihisa et al. | |
| 5,345,213 A | 9/1994 | Semancik et al. | |
| 6,634,210 B1 | 10/2003 | Bosch | |
| 7,954,230 B2 | 6/2011 | Nelson | |
| 2001/0035044 A1* | 11/2001 | Larsson et al. | 73/28.01 |
| 2005/0103772 A1* | 5/2005 | Streit et al. | 219/497 |
| 2008/0282769 A1 | 11/2008 | Nelson | |
| 2008/0283398 A1 | 11/2008 | Nelson et al. | |
| 2009/0056416 A1* | 3/2009 | Nair et al. | 73/28.01 |
| 2009/0126458 A1 | 5/2009 | Fleischer et al. | |
| 2009/0139081 A1 | 6/2009 | Nelson | |
| 2010/0147052 A1 | 6/2010 | Nelson et al. | |
| 2011/0048106 A1* | 3/2011 | Zawacki et al. | 73/28.01 |
| 2011/0109331 A1* | 5/2011 | Nelson et al. | 324/693 |
| 2011/0197571 A1* | 8/2011 | Visser et al. | 60/311 |

(Continued)

FOREIGN PATENT DOCUMENTS

| | | |
|---|---|---|
| EP | 1921430 A1 | 5/2008 |
| FR | 2926368 A1 | 7/2009 |

*Primary Examiner* — Quang D Thanh
*Assistant Examiner* — James Sims, III
(74) *Attorney, Agent, or Firm* — Joshua M. Haines

(57) ABSTRACT

A method for determining the temperature of a sensor that comprises a heater is provided. The method includes the steps of applying a voltage to the heater and measuring the voltage applied to the heater and the current through the heater during a first time interval, and removing the applied voltage from the heater and leaving the heater unpowered for a second time interval. The method further includes the steps of calculating the resistance of the heater using the measured voltage and current, and determining the temperature of the sensor from the resistance using a predetermined relationship. The first time interval is selected to be sufficiently short in duration and the second time interval is selected to be sufficiently long so as to not significantly raise the temperature of the heater. The sensor temperature so determined can be used to perform diagnostic functions for a system that includes the sensor.

1 Claim, 6 Drawing Sheets

(56) References Cited

U.S. PATENT DOCUMENTS

2011/0203348 A1\* 8/2011 Hedayat et al. ............. 73/23.33
2012/0056112 A1    3/2012 Bitter et al.

\* cited by examiner

TEMPERATURE MEASUREMENT METHOD FOR A HEATED SENSOR

BACKGROUND OF THE INVENTION

This invention relates generally to sensors which are used to detect electrically conductive particulate matter, such as soot, and more particularly to a method and system for diagnosing potential failure modes in such sensors.

Incomplete combustion of certain heavy hydrocarbon compounds, such as heavy oils, diesel fuel, and the like may lead to particulate formation (e.g., soot). In the operation of internal combustion engines, excessive particulate formation can lead to "smoking" of the engine, which causes air pollution even though the carbon monoxide, hydrocarbons, and other pollutant components of the gaseous state exhaust emissions may be relatively low. Emission regulations require many engines to limit the levels of particulate emissions, and various control technologies such as diesel particulate filters (DPF) have been employed for this purpose.

In order to monitor the emissions of particulate matter (PM) in the exhaust stream of certain types of internal combustion engines, e.g., to assess the effectiveness of DPF's, it is common practice to provide a particulate sensor system for detecting the level of particulate concentration emitted from an exhaust gas. Various particulate sensors have been proposed, including those shown in U.S. Pat. No. 4,656,832 issued to Yukihisa et al., U.S. Pat. No. 6,634,210 issued to Bosch et al., U.S. Pat. Publ. No. 2008/0283398 A1, U.S. Pat. Publ. No. 2008/0282769 A1, U.S. Pat. Publ. No. 2010/0147052 A1, and U.S. Pat. No. 7,954,230 issued to Nelson, the disclosures of each of which are hereby incorporated by reference in their entirety.

Particulate sensors (also referred to herein as PM sensors or soot sensors) such as those described above generally have a pair of spaced apart sensing electrodes disposed on a substrate. The sensing electrodes are coupled to a measurement circuit by way of electrically conductive leads. The operating principle of the particulate sensor is based on the conductivity of the particulates (e.g., soot) deposited between (or over) the sensing electrodes. The electrical resistance between the sensing electrodes is relatively high when the sensor is clean but such resistance decreases as soot particulates accumulate. These sensors also have a heater that can be selectively activated to burn off the soot particulates to "reset" the sensor to a known, base "clean" state.

Government regulations require that the PM sensor have self diagnostics (i.e. On Board Diagnostics or OBD) capability to verify that it is functioning properly. Some of these diagnostics (such as sensor over temperature) require that the temperature of the sensor is known.

Accordingly, there is a need for particulate sensor diagnostics that can determine the temperature of the sensor using an existing sensor implementation, without adding an additional dedicated temperature sensor.

BRIEF SUMMARY OF THE INVENTION

In an aspect of the invention, a method for determining the temperature of a sensor that comprises a heater is presented. The method includes the steps of applying a voltage to the heater for a first time interval and measuring the voltage applied to the heater and the current through the heater during the first time interval. The method further includes the steps of removing the applied voltage from the heater and leaving the heater unpowered for a second time interval. The method further includes the steps of calculating the resistance of the heater using the measured voltage and the measured current, and calculating the temperature of the sensor from the resistance of the heater using a predetermined relationship between the temperature of the heater and the resistance of the heater. The first time interval is selected to be sufficiently short in duration and the second time interval is selected to be sufficiently long so as to not significantly raise the temperature of the heater. The sensor temperature so determined can be used, for example, to perform diagnostic functions for a system that includes the sensor.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION OF THE INVENTION

Figure 1:
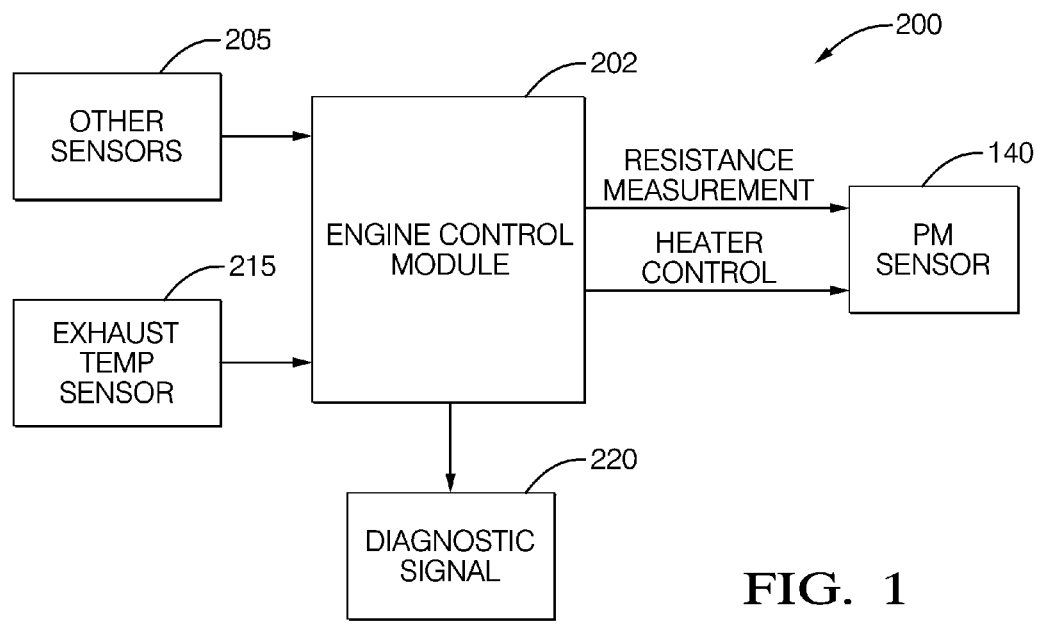
FIG. 1 is a block diagram of a vehicle system.

The method and system of the invention may be used in conjunction with a sensor that includes a heater in a variety of environments. In one exemplary embodiment, the sensor is a particulate matter (soot) sensor in the exhaust stream of an internal combustion engine such as a diesel engine. Referring now to FIG. 1, a non-limiting example of a particulate sensor diagnostic system 200 is illustrated, which includes a particulate matter sensor 140. The diagnostic system comprises a controller or an engine control module (ECM) 202. Alternatively to an ECM 202, a stand-alone diagnostic module or combined sensor and diagnostic control module may be used. ECM 202 comprises among other elements a microprocessor for receiving signals indicative of the vehicle performance as well as providing signals for control of various system components, read only memory in the form of an electronic storage medium for executable programs or algorithms and calibration values or constants, random access memory and data buses for allowing the necessary communication (e.g., input, output and within the ECM) with the ECM in accordance with known technologies.

In accordance with an exemplary embodiment the controller will comprise a microcontroller, microprocessor, or other equivalent processing device capable of executing commands of computer readable data or program for executing a control algorithm. In order to perform the prescribed functions and desired processing, as well as the computations therefore (e.g., the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include input signal filtering to enable accurate sampling and conversion or acquisitions of such signals from communications interfaces. As described above, exemplary embodiments of the present invention can be implemented through computer-implemented processes and apparatuses for practicing those processes.

The ECM 202 receives various signals from various sensors in order to determine the state of the engine as well as vary the operational state and perform diagnostics. For example, the ECM 202 can determine, based on its input from other sensors 205 and logic and control algorithms whether the engine is being started in a "cold start" state as well as perform and/or control other vehicle operations. Some of the sensors that may be included in the "other sensors" 205 which provide input to the ECM 202 include but are not limited to the following: engine coolant temperature sensor, engine speed sensor, exhaust oxygen sensor, and the like. The sensors used may also be related in part to the type of engine being used (e.g., water cooled, air cooled, diesel, gasoline, hybrid, etc.). The ECM 202 also receives input from exhaust temperature sensor 215, which may be a temperature probe located in the exhaust stream in proximity to the particulate matter sensor or other equivalent means or method for measuring the exhaust temperature.

In accordance with operating programs, algorithms, look up tables and constants resident upon the microcomputer of the ECM various output signals, including control of the heater element 160 (shown in FIG. 3 and FIG. 4) are provided by the ECM. While the control signal for the heater element 160 is relevant to the practice of the invention, the ECM may also provide other control signals to control the engine (e.g., limiting or shutting off fuel flow as well as closing or opening the intake and exhaust valves of the engine) as well as performing other vehicle operations including but not limited to: fuel/air flow control to maintain optimum, lean or rich stoichiometry as may be required to provide the required torque output; spark timing; engine output; and providing on board diagnostic (OBD) means to the vehicle operator.

Figure 2:
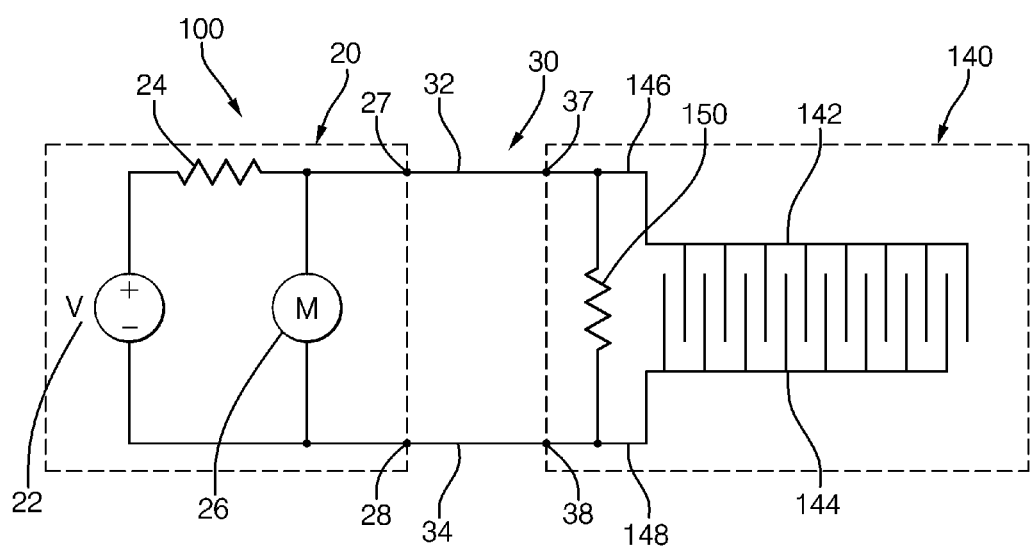
FIG. 2 is an electrical schematic of a portion of a soot sensing system.

FIG. 2 is an electrical schematic of a particulate matter sensing system 100 incorporating a bias resistor, as disclosed in U.S. patent application Ser. No. 12/947,867 filed Nov. 17, 2010 titled "SELF DIAGNOSTICS OF A PARTICULATE MATTER SENSOR", the contents of which are incorporated by reference in their entirety. The system may be generally considered as partitioned as indicated into a controller portion 20, a wiring harness portion 30, and a sensing element portion 140. The controller portion 20 comprises a means for measuring the impedance of a circuit connected thereto. In the exemplary controller portion 20 in FIG. 1, the impedance measurement means includes a voltage source 22 that provides a voltage value $V_{supply}$, a pull-up resistor 24 having a resistance value $R_{pullup}$, and a voltage measurement means 26. The controller portion 20 electrically interfaces to the wiring harness portion 30 by connection means 27 and 28. The wiring harness portion 30 includes conductors 32 and 34. The wiring harness portion 30 electrically interfaces to the sensing element portion 140 by connection means 37 and 38. The sensing element portion 140 includes a first electrode 142 electrically connected by conductor 146 to connection means 37, and a second electrode 144 electrically connected by conductor 148 to connection means 38. The sensing element portion 140 in FIG. 2 contains an additional bias resistor 150 having a resistance value of $R_{bias}$ electrically connected between conductors 146 and 148. The resistance of the sensing element $R_{sensor}$ as measured between connection means 37 and connection means 38 is the parallel combination of $R_{bias}$ and the resistance resulting from particulate matter bridging the gap between the first electrode 142 and the second electrode 144. $R_{sensor}$ can be represented mathematically as:

$$R_{sensor} = \frac{R_{bias} \times R_{particulate}}{R_{bias} + R_{particulate}}$$

In the absence of particulate matter on sensing element 140, the term $R_{particulate}$ is very large compared to $R_{bias}$, and the effective sensor resistance $R_{sensor}$ is essentially equal to $R_{bias}$. This condition provides the maximum resistance value of $R_{sensor}$. As particulate matter accumulates so as to bridge the gap between the first electrode 142 and the second electrode 144, the effective sensor resistance $R_{sensor}$ will decrease from its maximum value of $R_{bias}$.

For the particulate matter sensing system 100 depicted in FIG. 2, the voltage measured by measurement means 26 will be:

$$V_{measured} = V_{supply} \frac{R_{sensor}}{R_{pullup} + R_{sensor}}$$

In the absence of particulate matter, the value of $R_{sensor}$ will be at its maximum and will essentially equal $R_{bias}$. Under this condition, the voltage measured by measurement means 26 will be:

$$V_{measured} = V_{supply} \frac{R_{bias}}{R_{pullup} + R_{bias}}$$

Figure 3:
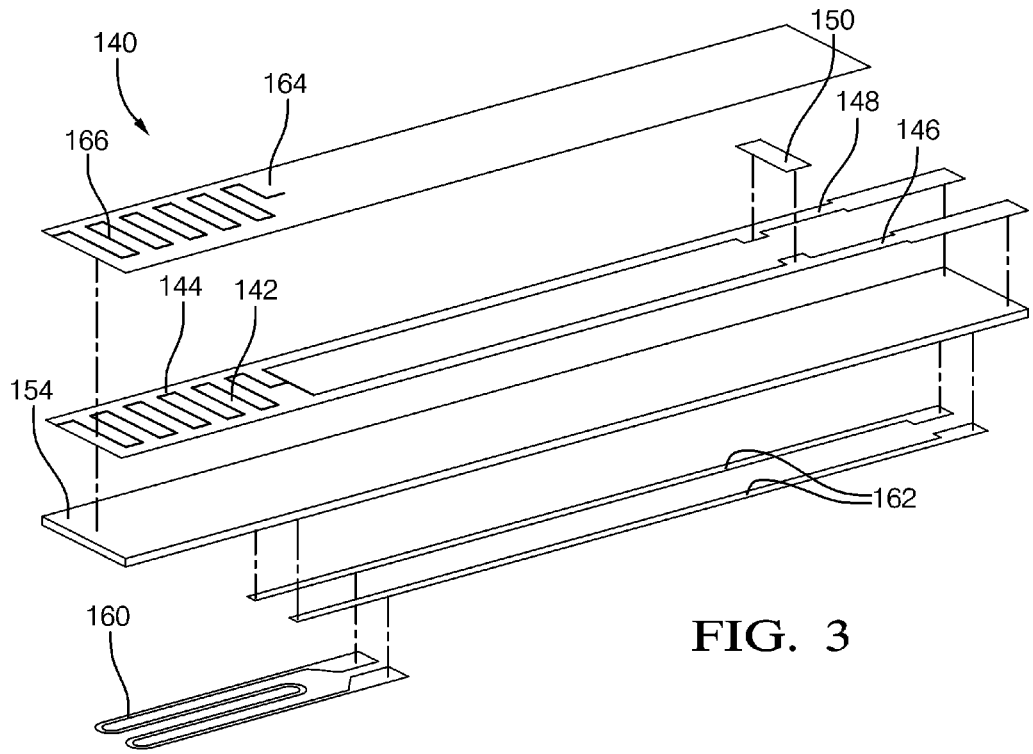
FIG. 3 is an exploded view of a soot sensor.

FIG. 3 is an exploded perspective view of the sensing element 140 of FIG. 2. The sensing element 140 includes an electrically insulating substrate 154. While shown as a single layer, it will be appreciated that substrate 154 may be formed by laminating together a plurality of layers. Conductive material disposed on one surface of substrate 154 is patterned to form conductors 146 and 148 and electrodes 142 and 144. Resistor material to form bias resistor 150 is deposited so as to form a resistive path between conductors 146 and 148. A protective layer 164 may also be included to protect the conductive material that forms electrodes 142 and 144, as well as portions of the conductors 146, 148 that may be exposed to abrasive particles in the gas stream being measured. The protective layer 164 includes an open area 166 exposing the gap between the electrodes 142 and 144 to allow particulate matter to bridge the electrodes 142 and 144. The protective layer 164 may also extend to cover bias resistor 150.

A particulate matter sensor may also include a heating means 160 that is controllable to raise the temperature in the vicinity of the electrodes 142, 144 on the sensing element. Raising the temperature sufficiently for a sufficient duration of time will result in particulate matter being removed from the surface of the sensing element, thereby restoring the resistance of the area between the sensing electrodes 142, 144 to a high resistance or essentially open circuit condition. This open circuit condition appears electrically in parallel with the bias resistor 150, so that the total resistance measured between connection means 37 and connection means 38 is restored to $R_{bias}$. The sensing element 140 depicted in FIG. 3 includes a heater 160 and heater leads 162, on the opposite surface of the substrate from the electrodes 142, 144. The heater 160 is positioned to allow the heater 160 to clean the particulate matter from the vicinity of the electrodes 142, 144 when the heater 160 is electrically powered by supplying current through heater leads 162.

The heater 160 is disposed between some of the nonconductive substrate layers and is provided to increase the temperature of the soot sensing element to be within a desired temperature range. In particular, the heater 160 generates heat in response to a signal received from the ECM 202. In one exemplary embodiment, the heater 160 can also periodically increase the temperature of the soot sensor 140 to at least 550 degrees Celsius to burn off the collected soot on the soot sensor 140. The heater 160 can also be energized to a higher temperature to burn off other contaminants that may be present on the soot sensor, as disclosed in commonly owned U.S. patent application Ser. No. 13/172,949 titled METHOD AND SYSTEM FOR CONTAMINATION REMOVAL FROM A PARTICULATE MATTER SENSOR filed on Jun. 30, 2011, which is herein incorporated by reference in its entirety. The aforementioned temperatures are merely provided as examples, and exemplary embodiments of the present invention are not intended to be limited to the specific temperature ranges provided herein.

Figure 4:
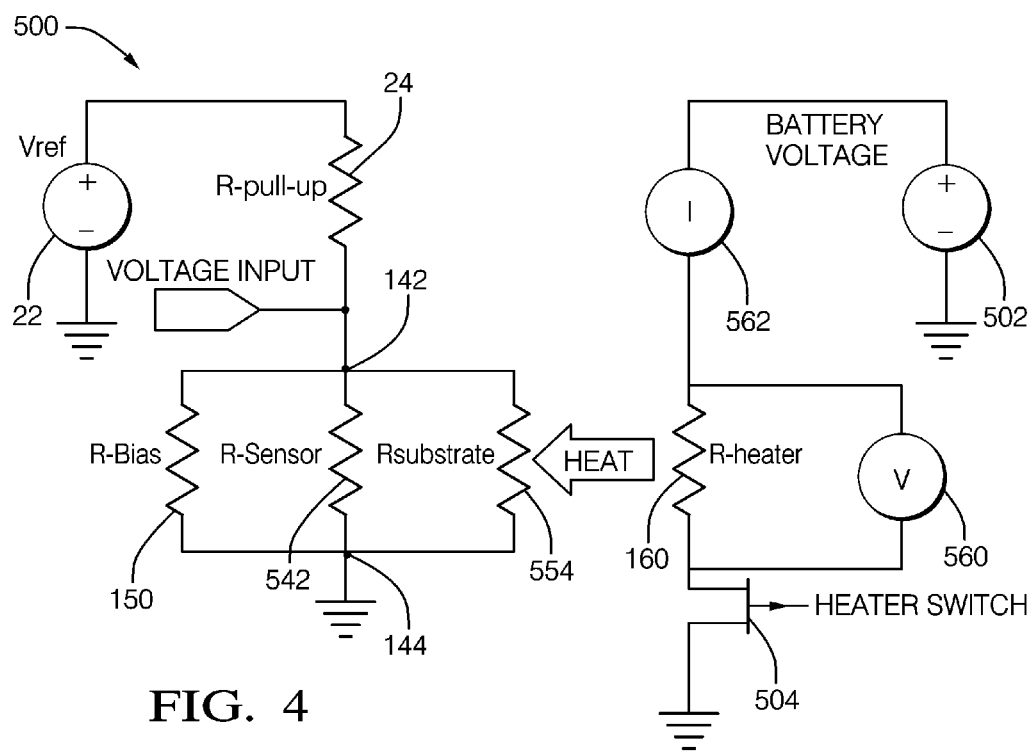
FIG. 4 is an electrical schematic that includes aspects of the present invention.

Referring now to FIG. 4, a non-limiting example of a particulate sensor system 500 is illustrated. The system includes a reference voltage source 22, a pull-up resistor 24, a bias resistor 150, and an arrangement for measuring the voltage across electrodes 142, 144. As shown in FIG. 4, voltage across the electrodes 142, 144 is dependent on the resistance between these electrodes. This resistance can be viewed as the parallel combination of three resistances, identified in FIG. 5 as 150, 542, and 554. Resistance 150 is the bias resistor, resistance 542 represents the resistance of material deposited between the sensing electrodes 142 and 144, and resistance 554 represents the resistance contribution of the material that comprises substrate 154 in FIG. 3, as measured between electrodes 142 and 144. The substrate typically has a high resistivity such that resistance 554 can for most purposes be ignored, that is, treated as an open circuit.

FIG. 4 also includes a voltage source 502 configured to deliver energy to heater 160 when heater switch 504 is turned on in response to a control signal commanding the heater to turn on. The heater may be provided with a pulse width modulated (PWM) heater drive voltage, for example with full battery voltage applied to the heater for an "on time" period, and essentially zero volts applied to the heater for an "off time" period. The duty cycle, defined as (on_time)/(on_time+off_time), can be controlled to achieve the desired sensor temperature. The "effective" heater voltage is approximately equal to the full battery voltage times the duty cycle percentage.

To provide diagnostic capability for a PM sensor, it is useful to be able to determine the temperature of the PM sensor. A dedicated temperature sensor, for example a resistance temperature detector (RTD), may be incorporated into the sensor. However, this would require additional materials and processing steps for the sensor, as well as additional connection means to the sensor and additional wires leading from the sensor to the resistance determining means.

In a non-limiting example, the heater 160 comprises platinum metal. Platinum has a resistance vs. temperature characteristic that makes it useful as an RTD. To measure the resistance of an RTD a voltage can be applied across the RTD which induces a current through the RTD. The resistance of the RTD can then be determined as the ratio of the voltage divided by the current. By Ohm's Law, the power P dissipated in a resistance R due to an applied voltage V can be determined as $P=V^2/R$. For a given voltage, the power dissipation is inversely proportional to the resistance. This power dissipation P will act to raise the temperature of the device, thereby affecting the temperature measurement. RTD devices typically have a resistance of several hundred ohms to minimize the self-heating of the device due to the power dissipation in the device during the resistance measurement process. In contrast, to achieve the desired heater temperature with the voltage that is typically available in a motor vehicle (nominally 12 volts), the heater 160 typically has a resistance of about 5 ohms. The very act of measuring the resistance of the heater 160 can result in tens of watts of power being dissipated in the heater 160, thereby affecting the temperature of the heater.

The method of an embodiment of the invention allows the heater 160 to be used as a temperature indicator in spite of the fact that the heater resistance is so low. Still referring to FIG. 4, a voltage measurement means 560 is provided to measure the voltage applied to the heater, and a current measurement means 562 is provided to measure the current flowing through the heater. The voltage measured by the voltage measurement means 560 and the current measured by the current measurement means 562 are used in the method described in FIG. 5 and FIG. 6.

Figure 5:
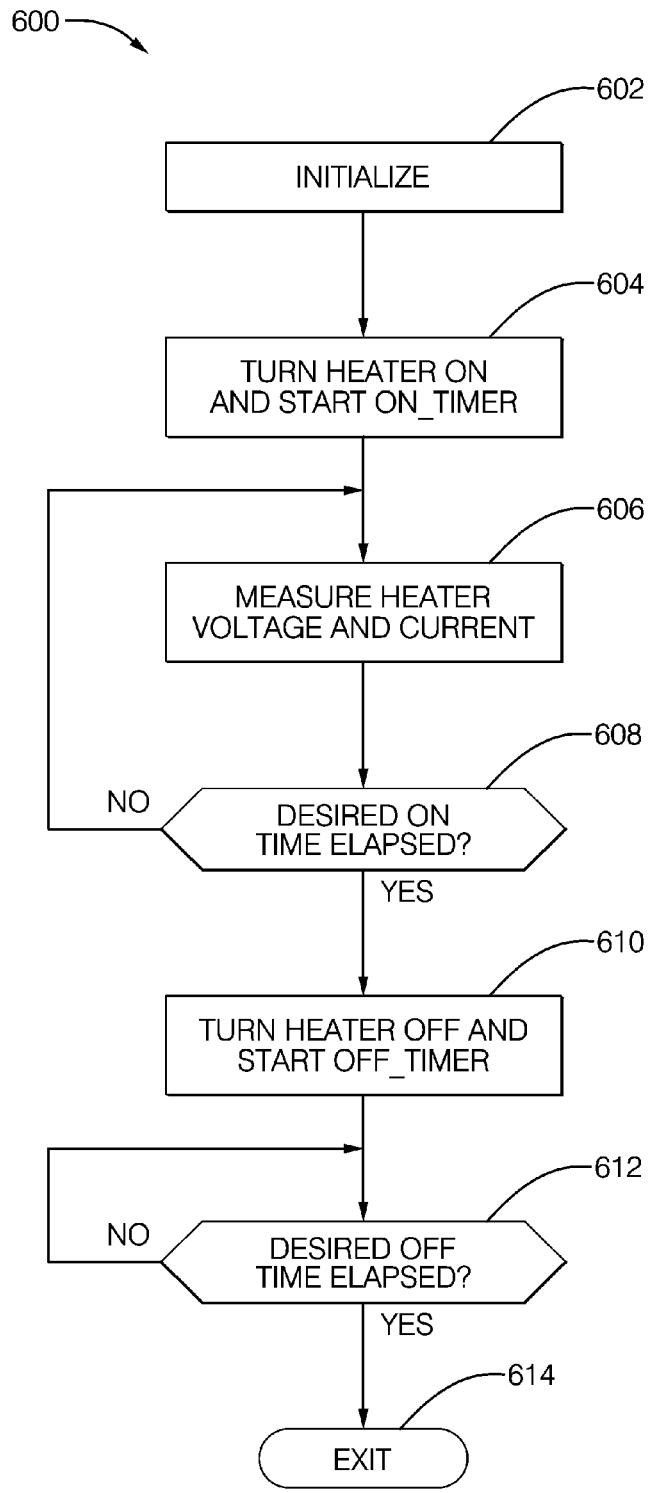
FIG. 5 is a flow chart depicting aspects of the present invention.

FIG. 5 depicts a flow chart of a method 600 for determining the temperature of the heater 160 during time intervals when the heater would not otherwise be energized. In method step 602, variables are set to desired initial values. The method then proceeds to step 604, where the heater 160 is turned on (for example, by actuating heater switch 504 shown in FIG. 4), and an on_timer is started. The method then proceeds to step 606, where the heater voltage and the heater current are measured (for example, by the voltage measurement means 560 and the current measurement means 562 shown in FIG. 4). The method proceeds to step 608, where the on_timer is evaluated to determine if the heater 160 has been on for the desired time. If the heater 160 has not been turned on for the desired on time, the method loops back to step 606. If the desired heater on time has elapsed, the method proceeds to step 610. In step 610, the heater is turned off (for example by turning off heater switch 504 shown in FIG. 4), and an off_timer is started. The method proceeds to step 612, where the off_timer is evaluated to determine if the heater 160 has been off for the desired time. If the heater 160 has not been turned off for the desired off time, the method loops back to the entry to step 612. If the desired heater off time has elapsed, the method proceeds to step 614 which provides an exit from method 600.

The heater voltage and heater current measurements obtained in step 606 can be used to determine a value for heater resistance. In one non-limiting embodiment, a single voltage measurement (for example, the voltage measurement obtained the last time that step 606 was executed) can be divided by a single current measurement (for example, the current measurement obtained the last time that step 606 was executed) to determine a calculated heater resistance. In another non-limiting embodiment, a plurality of voltage measurements and a plurality of current measurements obtained during a plurality of executions of step 606 can each be averaged, and the resulting average voltage value can be divided by the resulting average current value to determine an averaged heater resistance. In a particularly advantageous embodiment, the plurality of voltage measurements and the plurality of current measurements used in the determination of an averaged heater resistance will not include measurements taken immediately after the heater is turned on in step 604.

The resistance vs. temperature characteristic of a metal can generally be modeled as a polynomial function. For example, a second order polynomial can be used to approximate the resistance vs. temperature relationship as $R(T)=R_0(1+\alpha T+\beta T^2)$, where R(T) represents the resistance at a temperature of T degrees C., $R_0$ is the resistance at 0 degrees C., and $\alpha$ and $\beta$ are coefficients characteristic of the particular metal. Once a resistance value for the heater 160 has been determined, this resistance can be used as an indication of the temperature of the heater 160. The corresponding temperature can be determined from the calculated resistance using means known in the art, such as direct calculation or using a look-up table. The effective values of $\alpha$ and $\beta$ in the relationship above may not correspond directly to the values associated with the metal that comprises the heater 160. The voltage and current measurements obtained in step 606 include not only the effects of the heater 160, but also the resistance contributions of any wiring and interconnects between the measurement means 560, 562 and the heater 160. The wiring and interconnects may be at different temperatures than the temperature of the sensor 140. Additionally, the method of fabricating the heater 160 on the sensor 140 may result in temperature coefficient of resistance (TCR) values that differ from the bulk TCR of the metal that comprises the heater. Accordingly, it is advantageous to determine the relationship between heater temperature and indicated heater resistance for a particular application, and to use this predetermined relationship to create coefficient values and/or look-up table values to be used to relate resistance to temperature.

In method 600, the application of voltage to the heater 160 that is necessary to allow current measurement and corresponding resistance determination imparts electrical energy to the heater 160, resulting in temperature rise of the heater 160. To minimize the effect of self-heating of the heater 160 during the voltage and current measurement, the heater on time is chosen to be sufficiently short and the heater off time is chosen to be sufficiently long. It will be appreciated that the selection of on-time and off-time for the heater affects not only self-heating of the heater but also the effective rate at which temperature estimates can be updated.

Figure 6:
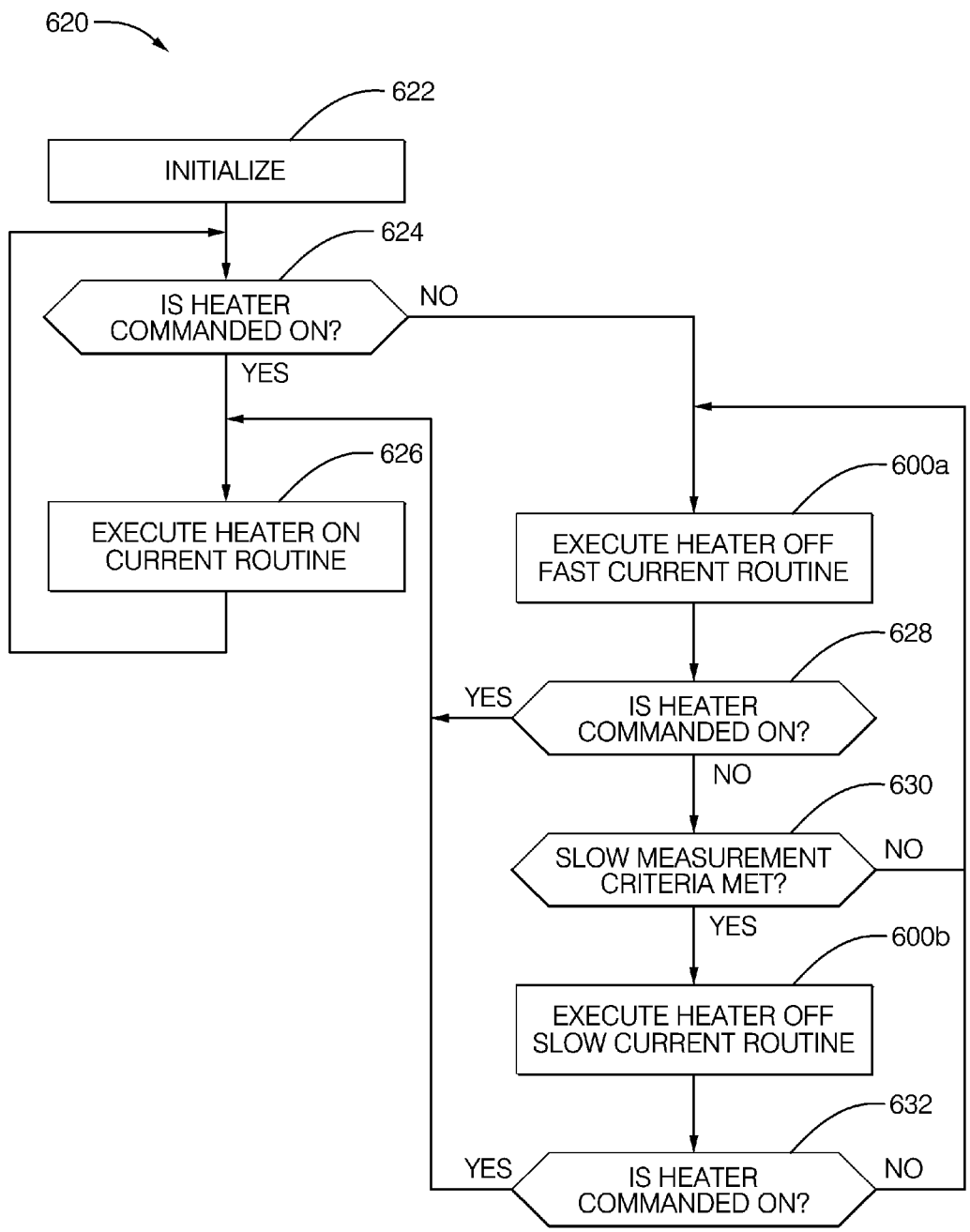
FIG. 6 is a flow chart depicting further aspects of the present invention.

In a further aspect of the present invention, the heater on time and heater off time in method 600 of FIG. 5 may be set to different values depending on an operating parameter of the system 200 in which the sensor 140 is used. Referring to FIG. 6, a method 620 is depicted. In step 622, values of variables are initialized. The method then proceeds to step 624, where a determination is made whether the heater 160 is commanded to an "on" state. Such a command may, for example, be issued when a determination is made to burn particulate matter off of the sensor 140. If the heater 160 is commanded to be on, the method proceeds to step 626, where a duty cycle is applied to heater switch 504, and heater voltage and current may simply be measured to determine the temperature of the heating element while the heater is on. The method proceeds from step 626 back to step 624.

If the determination in step 624 is that the heater 160 is not commanded to be on, the method proceeds to step 600a. In step 600a the steps of method 600 depicted in FIG. 5 are executed, with the durations of the on timer and the off timer selected for relatively fast execution of step 600a. Upon completion of step 600a, the method then proceeds to step 628, where a determination is made whether the heater 160 is commanded to an "on" state. If the heater 160 is commanded to be on, the method proceeds to step 626. If the determination in step 628 is that the heater 160 is not commanded to be on, the method proceeds to step 630. In step 630, a determination is made whether criteria are met for slow current measurement. If the criteria for slow current measurement (to be discussed below) are not met, the method proceeds back to step 600a. If the criteria for slow current measurement are determined to be met in step 630, the method proceeds to step 600b. In step 600b the steps of method 600 depicted in FIG. 5 are executed, with the durations of the on timer and the off timer selected for relatively slow execution of step 600b, when compared to the durations of the on timer and the off timer selected in step 600a. Upon completion of step 600b, the method then proceeds to step 632, where a determination is made whether the heater 160 is commanded to an "on" state. If the heater 160 is commanded to be on, the method proceeds to step 626. If the determination in step 632 is that the heater 160 is not commanded to be on, the method proceeds to step 600b.

The criteria used in step 630 to determine whether the fast current measurement routine 600a or the slow current measurement routine 600b should be used may be based on a parameter measured in the system 200. As a non-limiting example, the exhaust temperature in a vehicle system may be used as part of the criteria. For a particulate matter sensor mounted in a vehicle exhaust stream, the rate of change of temperature with respect to time will depend on the difference between the sensor temperature and the exhaust temperature. When this temperature difference is greatest, for example immediately after turning off the heater 160, the time rate of change of sensor temperature will be greatest. Under these conditions, it is advantageous to generate the temperature estimate with fast response time (i.e. to use the fast current measurement routine 600a), in order to keep up with the rapidly changing temperature. In addition to a vehicle system parameter being used in step 630 to determine whether the fast current measurement routine 600a or the slow current measurement routine 600b should be used, the durations of the on timer and the off timer used in measurement routine 600a may be adjusted in response to the value of a vehicle system parameter. For example, it has been determined to be advantageous to use short durations for the on timer and the off timer during rapid engine accelerations that quickly change the exhaust temperature.

As the sensor 140 cools to near the exhaust temperature, the sensor temperature changes more slowly, and a slower response time for the temperature determination may be adequate. In a particularly advantageous embodiment, the slow current measurement routine 600b is executed if the calculated sensor temperature is at or below a predetermined temperature offset from the exhaust temperature, and if the exhaust temperature is above a predetermined minimum exhaust temperature.

Figure 7:
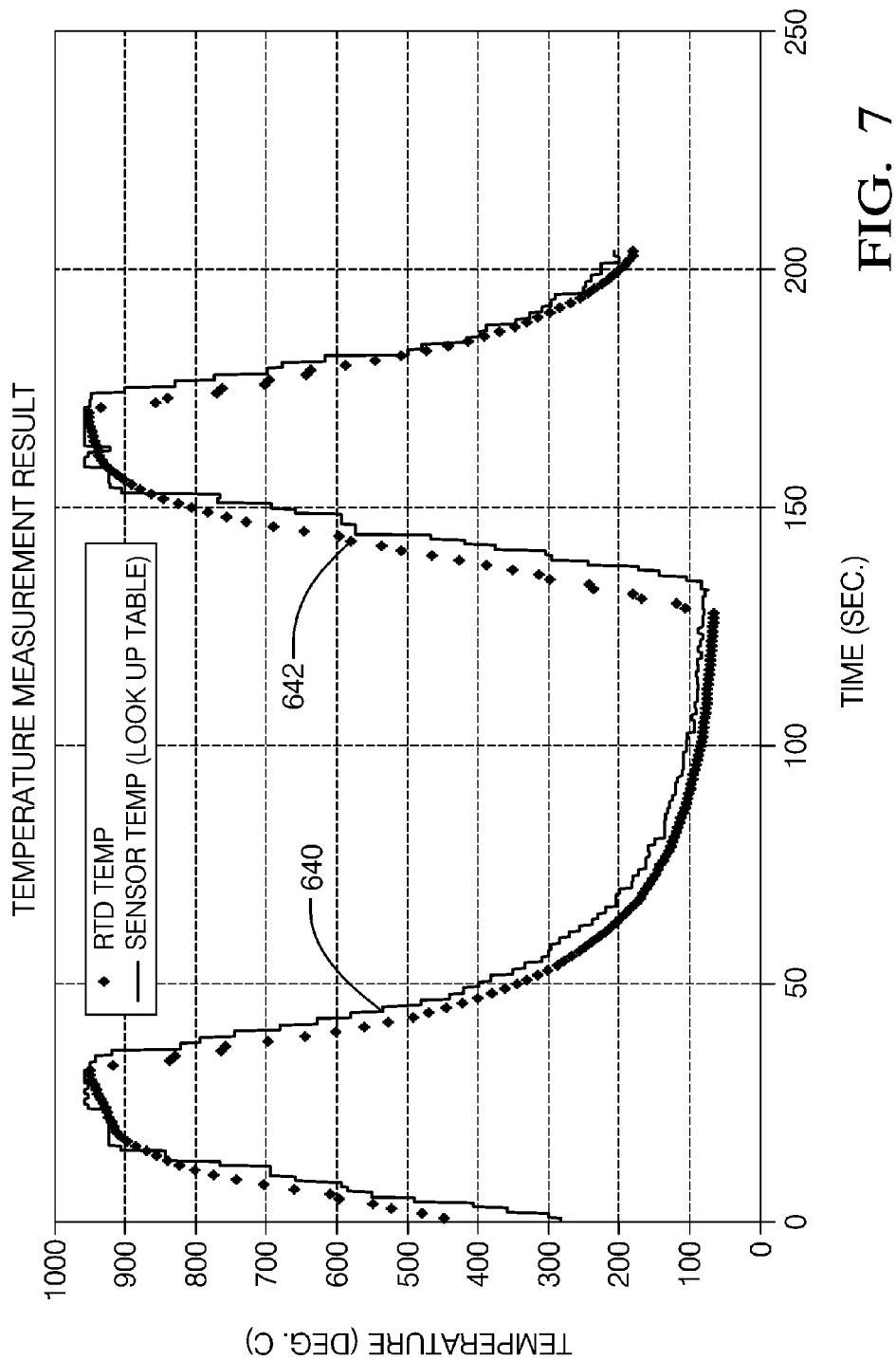
FIG. 7 is a chart showing temperature calculated using an aspect of the invention compared to temperature measured using an RTD.

FIG. 7 is a chart of sensor temperature vs. time for two on-off cycles of a heater. The time intervals where increasing temperature is indicated correspond to time intervals where the heater 160 is commanded on as in step 626 of FIG. 6, and the time intervals where the temperature is decreasing correspond to time intervals where the heater 160 is commanded on only for the brief time intervals required to execute step 604 through step 608 in FIG. 5. In FIG. 7, the solid line 640 represents the results of calculating sensor temperature using aspects of the method described herein, and the non-connected data points 642 represent the temperature as measured by a dedicated RTD on the sensor.

Figure 8:
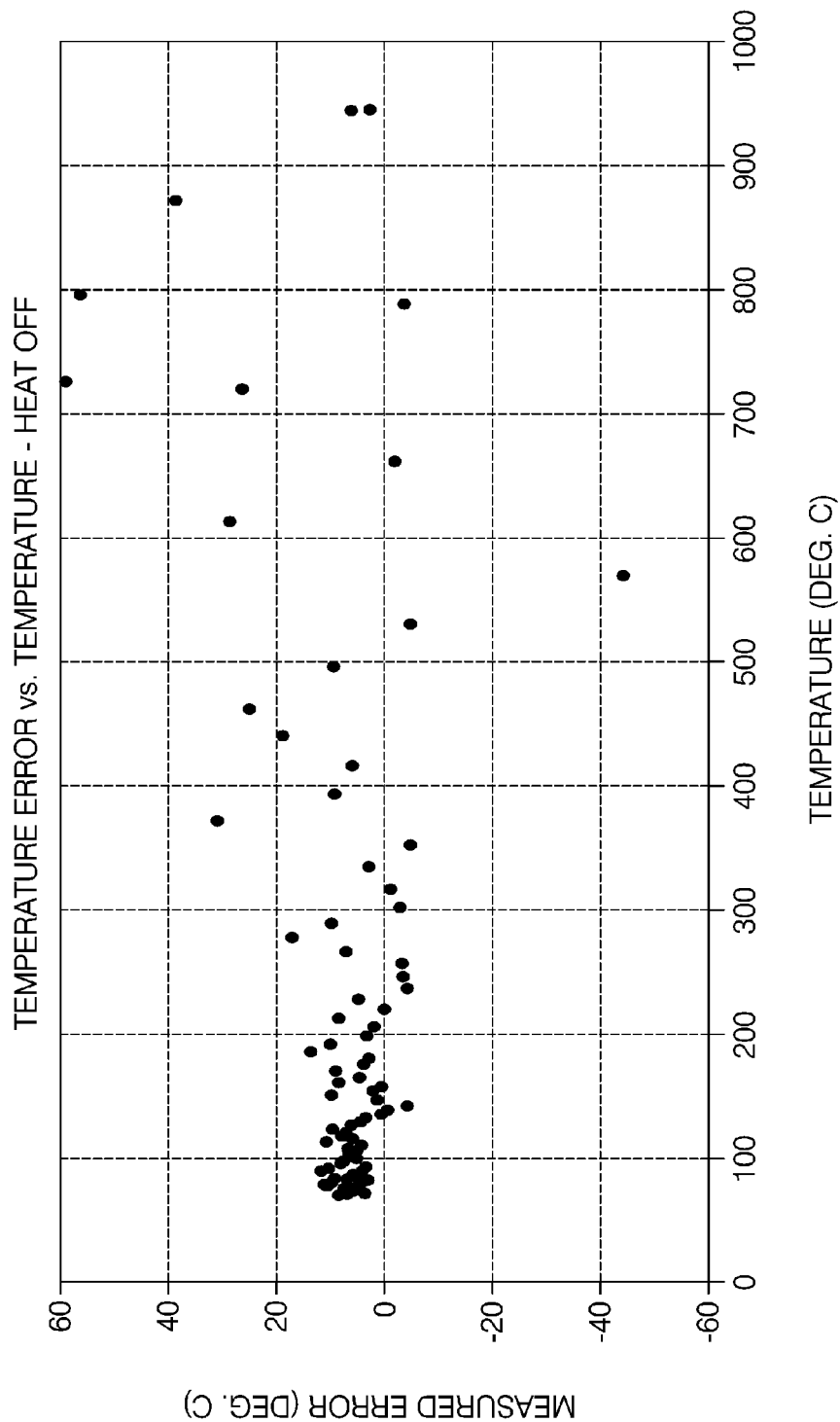
FIG. 8 is a chart showing the difference between measured temperature and temperature calculated using an aspect of the invention.

FIG. 8 is a plot of the difference between the calculated temperature and the measured temperature, plotted against the measured temperature, for the portions of FIG. 7 where the temperature is decreasing, that is, for the time intervals where the heater is not commanded on.

The temperature information provided by the method of the present invention may be used to support a variety of control and/or diagnostic functions. By way of non-limiting example, the temperature determined for the particulate matter sensor 140 may be compared to the temperature reported by the exhaust temperature sensor 215 for diagnostic purposes. In another non-limiting example, the temperature determined for the particulate matter sensor 140 may be evaluated to detect malfunctions in the heater control portion of the system 200.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but rather by the claims which follow.

The invention claimed is:

1. An apparatus comprising:
a processor, and
a memory storing instructions that, when executed, cause the apparatus to
(a) apply a voltage to a heater for a first time interval;
(b) measure the voltage applied to the heater and a current through the heater during the first time interval;
(c) remove the applied voltage from the heater;
(d) leave the heater unpowered for a second time interval;
(e) calculate a resistance of the heater using the measured voltage and the measured current;
(f) calculate a temperature of the heater from the resistance of the heater using a predetermined relationship between the temperature of the heater and the resistance of the heater;
wherein the first time interval is selected to be sufficiently short in duration and the second time interval is selected to be sufficiently long so as to not significantly raise the temperature of the heater.

* * * * *